United States Patent [19]
Boyce et al.

[11] Patent Number: 5,899,939
[45] Date of Patent: May 4, 1999

[54] BONE-DERIVED IMPLANT FOR LOAD-SUPPORTING APPLICATIONS

[75] Inventors: Todd M. Boyce, Aberdeen; Albert Manrique, Manalapan; Nelson L. Scarborough, Ocean; James L. Russell, Little Silver, all of N.J.

[73] Assignee: Osteotech, Inc., Eatontown, N.J.

[21] Appl. No.: 09/009,997

[22] Filed: Jan. 21, 1998

[51] Int. Cl.⁶ .................................................... A61F 2/28
[52] U.S. Cl. .............................. 623/16; 623/11; 523/113; 523/115
[58] Field of Search ........................ 623/11, 16; 523/113, 523/115

[56] References Cited

U.S. PATENT DOCUMENTS

| | | |
|---|---|---|
| 3,609,867 | 10/1971 | Hodosh . |
| 3,790,507 | 2/1974 | Hodosh . |
| 4,394,370 | 7/1983 | Jefferies . |
| 4,430,760 | 2/1984 | Smestad . |
| 4,440,750 | 4/1984 | Glowacki et al. . |
| 4,472,840 | 9/1984 | Jefferies . |
| 4,485,097 | 11/1984 | Bell . |
| 4,512,038 | 4/1985 | Alexander et al. . |
| 4,516,276 | 5/1985 | Mittelmeier et al. . |
| 4,623,553 | 11/1986 | Ries et al. . |
| 4,627,853 | 12/1986 | Campbell et al. ........................ 623/16 |
| 4,636,526 | 1/1987 | Dorman et al. . |
| 4,637,931 | 1/1987 | Schmitz . |
| 4,678,470 | 7/1987 | Nashef et al. . |
| 4,698,375 | 10/1987 | Dorman et al. . |
| 4,795,467 | 1/1989 | Piez et al. . |
| 4,842,604 | 6/1989 | Dorman et al. . |
| 4,932,973 | 6/1990 | Gendler . |
| 5,007,930 | 4/1991 | Dorman et al. . |
| 5,053,049 | 10/1991 | Campbell . |
| 5,071,436 | 12/1991 | Huc et al. . |
| 5,236,456 | 8/1993 | O'Leary et al. . |
| 5,298,254 | 3/1994 | Prewett et al. . |
| 5,306,302 | 4/1994 | Bauer et al. . |
| 5,306,304 | 4/1994 | Gendler . |
| 5,314,476 | 5/1994 | Prewett et al. . |
| 5,356,629 | 10/1994 | Sander et al. . |
| 5,425,769 | 6/1995 | Snyders, Jr. . |
| 5,425,770 | 6/1995 | Piez et al. . |
| 5,464,439 | 11/1995 | Gendler . |
| 5,507,813 | 4/1996 | Dowd et al. . |
| 5,522,895 | 6/1996 | Mikos . |
| 5,522,904 | 6/1996 | Moran et al. . |
| 5,531,791 | 7/1996 | Wolfinbarger, Jr. . |
| 5,556,430 | 9/1996 | Gendler . |
| 5,573,771 | 11/1996 | Geistlich et al. . |
| 5,585,116 | 12/1996 | Boniface et al. . |
| 5,645,591 | 7/1997 | Kuberasampath et al. . |
| 5,683,459 | 11/1997 | Brekke . |

*Primary Examiner*—Paul B. Prebilic
*Attorney, Agent, or Firm*—Dilworth & Barrese

[57] ABSTRACT

A bone-derived implant is provided which is made up of one or more layers of fully mineralized or partially demineralized cortical bone and, optionally, one or more layers of some other material. The layers constituting the implant are assembled into a unitary structure to provide an implant exhibiting good overall load-supporting properties.

33 Claims, 3 Drawing Sheets

BONE-DERIVED IMPLANT FOR LOAD-SUPPORTING APPLICATIONS

BACKGROUND OF THE INVENTION

1. Technical Field

The present invention relates to a bone-derived implant fabricated at least in part from strength-imparting cortical bone and intended for use in the repair, replacement and/or augmentation of various portions of animal or human skeletal systems. More particularly, this invention relates to a bone-derived implant which is made up of two or more layers at least one of which is fully mineralized or partially demineralized cortical bone and, optionally, one or more layers fabricated from some other material. The individual layers constituting the implant are assembled into a unitary structure capable of supporting loads.

2. Description of the Related Art

The use of autograft bone, allograft bone or xenograft bone is well known in both human and veterinary medicine. See Stevenson et al., *Clinical Orthopedics and Related Research*, 323, pp. 66–74 (1996). In particular, transplanted bone is known to provide support, promote healing, fill bony cavities, separate bony elements such as vertebral bodies, promote fusion and stabilize the sites of fractures. More recently, processed bone has been developed into shapes for use in new surgical applications, or as new materials for implants that were historically made of non-biologically derived materials.

U.S. Pat. No. 4,678,470 describes a non-layered bone grafting material produced from bone by a process which includes tanning with glutaraldehyde. The bone may be pulverized, used as a large block or machined into a precise shape. The tanning stabilizes the material and also renders it non-antigenic. The bone material may also be demineralized.

The use of a continuous sheet of demineralized bone or partially demineralized bone is described in U.S. Pat. No. 5,556,430; however, the sheet must be sufficiently flexible, therefore sacrificing strength, in order to conform to the skeletal site to which it is applied.

The surgically implantable sheet described in U.S. Pat. No. 5,507,813 is formed from elongate bone particles, optionally demineralized, containing biocompatible ingredients, adhesives, fillers, plasticizers etc.

U.S. Pat. No. 4,932,973 discloses an artificial organic bone matrix with holes or perforations extending into the organic bone matrix. These holes or perforations are indicated to be centers of cartilage and bone induction following implantation of the bone matrix.

U.S. Pat. No. 4,394,370 discloses a one-piece sponge-like bone graft material fabricated from fully demineralized bone powder or micro particulate bone, and reconstituted collagen. The sponge-like graft is optionally cross-linked with glutaraldehyde.

Another one-piece porous implant is described in U.S. Pat. No. 5,683,459. The implant is made up of a biodegradable polymeric macrostructure, which is structured as an interconnecting open cell meshwork, and a biodegradable polymeric microstructure composed of chemotactic ground substances such as hyaluronic acid.

SUMMARY OF THE INVENTION

The present invention provides a long felt need in the field by providing a bone-derived implant capable of supporting loads and, in a preferred embodiment, through its bone healing activity and ability to incorporate medically/surgically useful substances at a surgical site to promote and/or accelerate new bone growth.

It is therefore an object of the present invention to provide a bone-derived implant made up of a plurality of superimposed layers, fixed to each other into a unitary structure, and possessing compression strength characteristics approximating those of natural bone.

It is another object of the invention to provide a bone implant possessing a network of pores, apertures, perforations, channels or spaces which permits and encourages penetration by endogenous and exogenous bone healing materials and blood supply, and simultaneously provides a means for incorporating one or more bone healing substances.

It is yet a farther object of the present invention to provide a bone-derived implant which can be fashioned into a variety of shapes and sizes which are not limited by constraints imposed by the normal anatomical sizes and/or types of donor bone which are available for the construction of the implant.

In keeping with these and other objects of the invention, there is provided a bone-derived implant which comprises a plurality of superimposed layers assembled into a unitary structure, at least one layer in the structure being a compression-strength imparting layer fabricated from non-demineralized cortical bone or partially demineralized cortical bone.

The bone-derived implant of the present invention possesses a significant advantage over prior art bone and bone-derived implants in its ability to approximate the mechanical strength characteristics of natural bone and to permit gradual transfer of load-bearing support therefrom to newly formed bone tissue over time.

Another important advantage of the bone-derived implant herein over prior art implants lies in its ability to function as a carrier for, and effectively incorporate, one or more medically/surgically useful substances that promote new bone growth and/or accelerate healing.

The term "osteogenic" as used herein shall be understood to refer to the ability of a substance to induce new bone formation via the participation of living cells from within the substance.

The term "osteoconductive" as used herein shall be understood to refer to the ability of a substance or material to provide biologically inert surfaces which are receptive to the growth of new host bone.

The term "osteoinductive" as used herein shall be understood to refer to the ability of a substance to recruit cells from the host which have the potential for repairing bone tissue.

BRIEF DESCRIPTION OF THE DRAWINGS

Various embodiments are described below with reference to the drawings wherein.

DETAILED DESCRIPTION OF THE PREFERRED EMBODIMENTS

Figure 1:
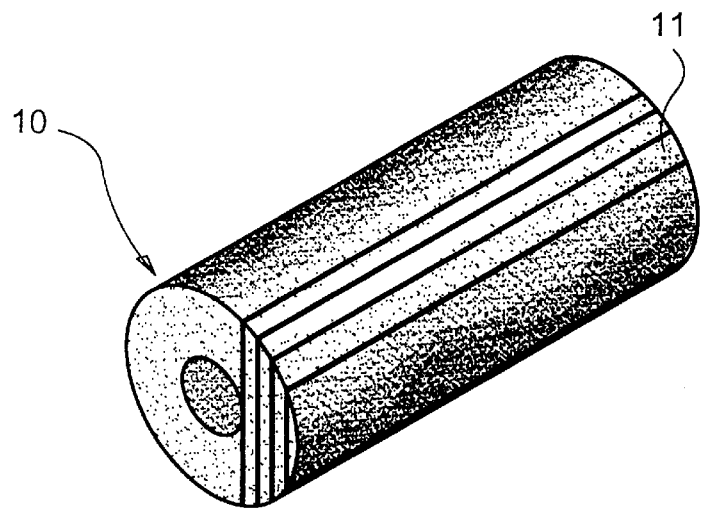
FIG. 1 is a cross-sectional view of bone from the diaphyseal region which has been sliced longitudinally into several cortical bone layers.

The bone-derived implant of the present invention comprises at least two superimposed layers at least one of the layers being a compression strength-imparting layer derived from nondemineralized cortical bone or cortical bone which has been only partially demineralized. When present as a compression strength-imparting layer, a partially demineralized cortical bone layer should exhibit a fairly high percentage of the compression strength of a comparable layer of nondemineralized cortical bone, e.g., preferably at least about 40, more preferably at least about 50 and still more preferably at least about 60 percent of such strength. Layers of partially demineralized cortical bone which exhibit significantly less than about 40 percent of the compression strength of a comparable layer of fully mineralized cortical bone can optionally be utilized in the bone-derived implant but in some capacity other than a load-bearing one. Depending on the thickness of the layers, there can be anywhere from 2 to about 200 layers overall in the bone-derived implant. The bone-derived implant can include layers of varying thicknesses, e.g., the compression strength-imparting layer(s) can be considerably thicker or thinner than any optional layer(s) that may be present. Thicknesses ranging from about 0.5 to about 20, and preferably from about 1.5 to about 15 mm can advantageously be used. In general, the number and thickness of the compression-strength imparting layers in a given bone-derived implant will be such as to provide an overall compression strength for the implant of from about 25 to about 250, and preferably from about 100 to about 200 MPa.

The sources of cortical bone for the bone-derived implant of this invention are preferably allogenic but also include xenogenic sources such as bovine and porcine bone. Where partially or fully demineralized cortical bone is utilized, such bone can be obtained employing known demineralization techniques, e.g., those employing strong acids such as hydrochloric acid as described in Reddi et al., *Proc. Nat. Acad. Sci.* 69, pp. 1601–5 (1972), herein incorporated by reference. The extent of demineralization is a function of the strength of the acid solution, the shape of the bone and the duration of the demineralization treatment. Reference in this regard may be made to Lewandrowski et al., *J. Biomed Materials Res*, 31, pp365–372 (1996), also incorporated herein by reference. The use of partially or fully demineralized bone can be beneficial herein since such substances exhibit greater initial osteogenic and/or osteoinductive activity than fully mineralized bone.

The compression strength-imparting layer(s) of the bone-derived implant can be provided as monolithic sections of bone or as multi-sectional layers built up from two or more subsections, e.g., joined to each other in edge-to-edge fashion in a manner which is analogous to planking. In this way, relatively large compression strength-imparting layers can be constructed from smaller bone sections to provide an implant whose overall size is not limited by the size and/or shape of the cortical bone which is available for its construction.

Assembling the superimposed layers into a strong unitary structure can be accomplished by a variety of means/procedures, e.g., application of known and conventional biologically compatible adhesives such as the cyanoacrylates; epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, etc., and protein-based binders such as fibrin glues and mussel-derived adhesive proteins; the use of mechanical fasteners such as pins, screws, dowels, etc., which can be fabricated from natural or synthetic materials and bioabsorbable as well as nonbioabsorbable materials; laser tissue welding; and, ultrasonic bonding. If desired, the layers of the bone-derived implant can be provided with mechanically interengaging features, e.g., tongue-and-groove or mortise-and-tenon elements, to facilitate their assembly into the final product and/or to fix the layers to each other in a more secured fashion. In addition to its compression strength-imparting fully mineralized or partially mineralized cortical bone layers, the bone-derived implant of this invention can optionally possess one or more layers formed from one or more other materials. For example, these optional layers can be based on or include highly or fully demineralized bone, graphite or pyrolytic carbon, a mineral material such as hydroxyapatite, tricalcium phosphate, bioglass or other bioceramic or natural or synthetic polymers, e.g., bioabsorbable materials such as starches, polyglycolide, polylactide, glycolide-lactide copolymer, and the like, and nonbioabsorbable polymers such as polymethyl methacrylate, polytetrafluoroethylene, polyurethane, polyethylene and nylon.

If desired, the compression strength axis of one or more compression strength-imparting layers can be offset relative to the compression strength axis of one or more of the other compression strength-imparting layers in an arrangement much like that of plywood. For example, compression strength axes of alternating compression strength-imparting layers can be offset by up to 90° from the compression strength axes of the other compression strength-imparting layers in the implant in order to distribute the overall load-supporting capacity of the implant in mutually transverse directions.

Bone-derived implants of any desirable size and/or configuration can be provided, e.g., by machining or other mechanical shaping operations such as press-molding. Computerized modeling of a specific implant followed by computerized control of the shaping of the implant can be used to provide an intricately shaped bone-derived implant which is custom-fitted to the intended site of application with great precision.

The bone-derived implant can possess one or more cavities which, if desired, can communicate with the surface of the implant through pores, apertures, perforations or channels provided for this purpose and ranging in average diameter from a few microns to several millimeters. Such cavities and their associated pores, apertures, perforations and channels can be partially or completely filled with one or more medically/surgically useful substances which promote or accelerate new bone growth or bone healing due, e.g., to some osteogenic, osteoconductive and/or osteoconductive effect. Useful substances of this kind which can be incorporated into the bone-derived implant of this invention include, e.g., collagen, insoluble collagen derivatives, etc., and soluble solids and/or liquids dissolved therein, e.g., antiviral agents, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; biocidal/biostatic sugars such as dextroal, glucose, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; collagen lattices; antigenic agents; cytoskeletal agents; cartilage fragments, living cells such as chondrocytes, bone marrow cells, mesenchymal stem cells, natural extracts, tissue transplants, bone, demineralized bone powder (or "demineralized bone matrix" as it may also be referred to), autogenous tissues such as blood, serum, soft tissue, bone marrow, etc.; bioadhesives, bone morphogenic proteins (BMPs), transforming growth factor (TGF-beta), insulin-like growth factor (IGF-1); growth hormones such as somatotropin; bone digesters; antitumor agents; immunosuppressants; permeation enhancers, e.g., fatty acid esters such as laureate, myristate and stearate monoesters of polyethylene glycol, enamine derivatives, alpha-keto aldehydes, etc.; and, nucleic acids. These and similar medically/surgically useful substances can be incorporated into the bone-derived implant of this invention or any of its constituent layers during any stage of the assembly of the implant. Suitable methods of incorporation include coating, immersion saturation, packing, etc. The amounts of medically/surgically useful substances utilized can vary widely with optimum levels being readily determined in a specific case by routine experimentation.

The bone-derived implant herein is intended to be applied at a bone defect site, e.g., one resulting from injury, defect brought about during the course of surgery, infection, malignancy or developmental malformation. The bone-derived implant, suitably sized and shaped as required, can be utilized as a graft or replacement in a wide variety of orthopaedic, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g., deficit filling, discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, etc. Specific bones which can be repaired or replaced with the bone-derived implant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones.

Referring to the drawings, as shown in FIG. 1, the cortical portion of bone 10 taken from the diaphyseal region is cut into cortical bone layers 11 of varying width by slicing the bone longitudinally. If desired, cortical bone layers 11 can be further cut to uniform size and shape as in bone layers 22 of the implant 20 shown in FIG. 2.

Figure 2:
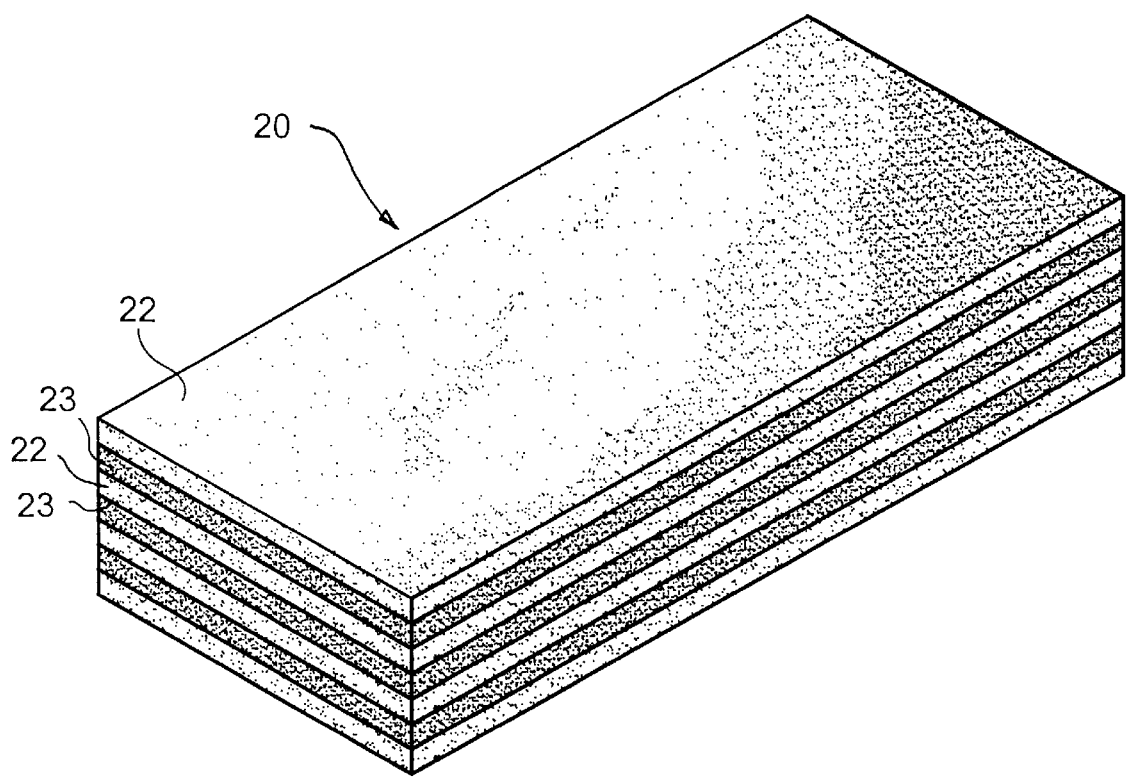
FIG. 2 is an enlarged perspective view of a bone-derived implant of the invention possessing layers of fully mineralized cortical bone alternating with layers of partially and/or fully demineralized cortical bone.

FIG. 2 illustrates a bone-derived implant 20 comprising alternating layers of fully mineralized cortical bone 22 and partially demineralized cortical bone 23. Alternatively, one or more layers 23 can be made from a material other than partially demineralized bone such as fully demineralized bone or mineral substances such as hydroxyapatite. The total thickness of the bone implant will ordinarily be at least about 5, and preferably at least about 10, mm. Bone-derived implant 20 can be cut, machined, and/or otherwise formed into any other desired shape or dimension for implantation into a body. For example, a substantially cylindrically shaped bone implant can be made for use as a long bone segment replacement, e.g., for a femur. To form a cylinder, a substantially square or rectangular bone-derived implant can be shaped on a lathe to the required diameter. A cavity can be formed by removing material with, for example, a drill, or, alternatively, a cavity can be formed by assembling appropriately configured layers.

Figure 3:
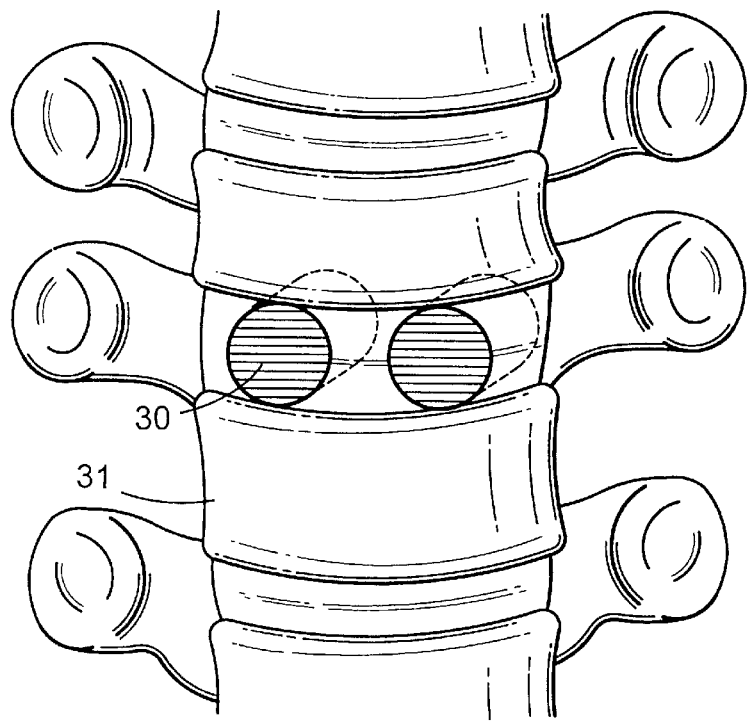
FIG. 3 is a partial view of the human vertebral column showing a dowel-shaped bone-derived implant of the invention installed at an intervertebral site.

As shown in FIG. 3, cylindrical or dowel-shaped bone-derived implant 30 is shown inserted at the intervertebral fibrocartilage site on the anterior side of vertebral column 31.

Figure 4:
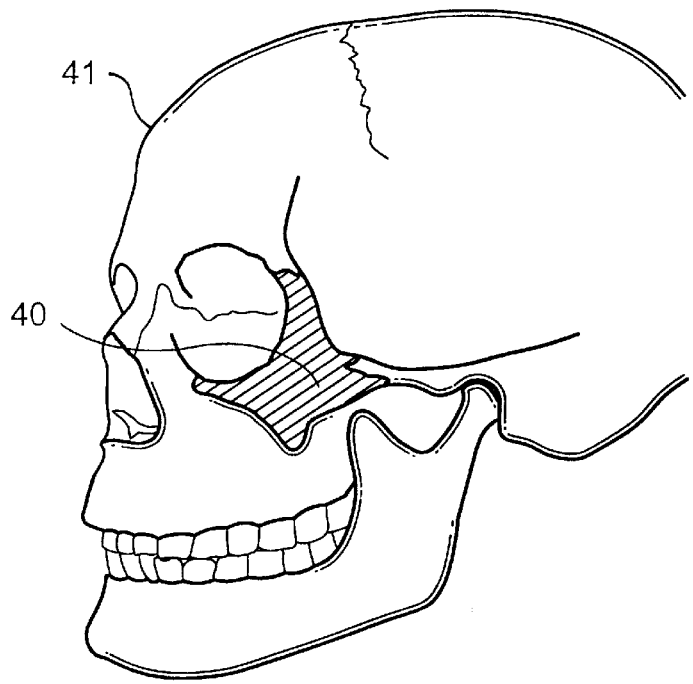
FIG. 4 is a view of the human skull showing a bone-derived implant of the invention fashioned as a zygomatic bone replacement.

In FIG. 4, zygomatic bone-derived implant 40 is sized and shaped to form part of the zygomatic arch and part of the interior orbit of skull 41.

Figure 6:
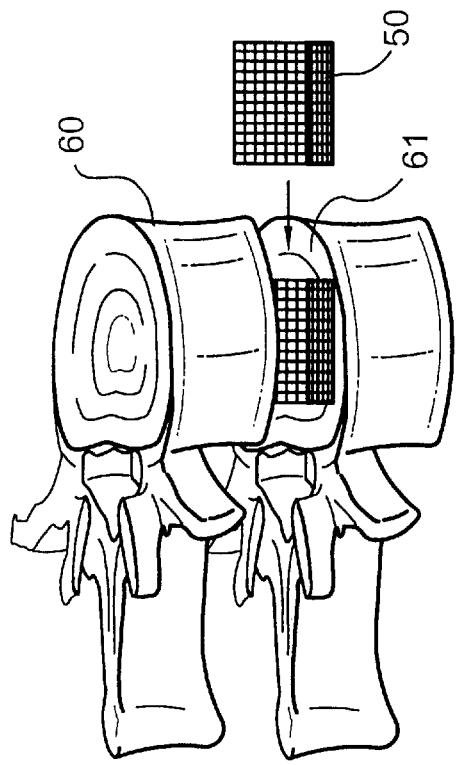
Figure 5:
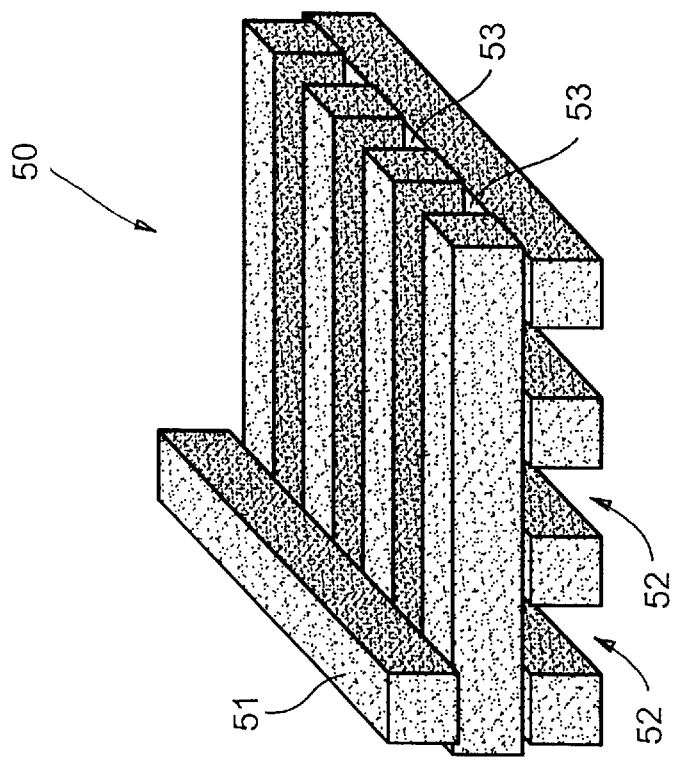
FIG. 5 is an enlarged perspective view of a lattice-like section of bone-derived implant; and, FIG. 6 is a partial view of the human vertebral column showing installation of the bone-derived implant of FIG. 5 at an intervertebral site.

As shown in the sectional view of FIG. 5, bone-derived implant 50 is built up from elongate sections 51 of compression strength-imparting fully mineralized or partially demineralized cortical bone of uniform square cross section and arranged in lattice-wise fashion employing a suitable adhesive, e.g., of the cyanoacrylate variety. Because of the open structure of implant 50 resulting from the pattern of longitudinal channels 52 and transverse channels 53, the implant permits the vascular penetration or host bone ingrowth therein and/or the diffusion of one or more medically/surgical useful substances therefrom. Vertical channels in the lattice-like array can, if desired, be partially or completely occupied by appropriately-configured and dimensioned sections 54 fabricated from fully mineralized or partially demineralized cortical-bone as in cortical bone sections 51 or from any of the other substances disclosed herein. Fully assembled bone implant 50 is shown installed in intervertebral space 61 of vertebral column 60 of FIG. 6.

The following examples are further illustrations of the bone-derived implant of this invention.

EXAMPLE 1

A cortical section of bone from the diaphyseal region was cut in the longitudinal direction while continuously wetted with water into approximately 1.5 mm thick layers using a diamond-bladed saw. The layers were then frozen to −70° C. and freeze-dried for 48 hours. The layers were then assembled with cyanoacrylate adhesive and held in a clamp for two hours while the adhesive set. The resulting multi-layered unitary structure was cut on a band saw and shaped by grinding and machining with a hand-held motorized shaping tool to provide a shaped bone implant.

EXAMPLE 2

A section of cortical bone from the diaphyseal region was saw-cut as in Example 1 into approximately 1.5 mm thick layers. Half of the slices were fully demineralized in a known manner employing 0.6N HCl acid. All of the layers were then assembled with cyanoacrylate adhesive with layers of fully mineralized bone alternating with layers of fully demineralized bone. A bone-derived implant of this type is illustrated in FIG. 2.

EXAMPLE 3

A diaphyseal bone segment about 50 mm in length was saw-cut while continuously wetted with water to provide elongate cortical bone sections of uniform, square cross section. The elongate bone sections were then assembled with cyanoacrylate adhesive to provide a lattice-like structure in which layers of spaced-apart bone sections were arranged transversally with respect to each other. A section of bone-derived implant of this type is illustrated in FIG. 5.

What is claimed is:

1. A bone-derived implant which comprises a plurality of superimposed layers assembled with an adhesive into a unitary structure, at least one layer in the structure being a compression strength-imparting layer fabricated from non-demineralized cortical bone or partially demineralized cortical bone.

2. The bone-derived implant of claim 1 wherein the partially demineralized bone exhibits not less than about 40 percent of the compression strength of a comparable layer of fully mineralized bone.

3. The bone-derived implant of claim 1 wherein the partially demineralized bone exhibits not less than about 50 percent of the compression strength of a comparable layer of fully mineralized bone.

4. The bone-derived implant of claim 1 wherein the partially demineralized bone exhibits not less than about 60 percent of the compression strength of a comparable layer of fully mineralized bone.

5. The bone-derived implant of claim 1 possessing at least two compression strength-imparting layers.

6. The bone-derived implant of claim 1 possessing a total thickness of at least about 5 mm.

7. The bone-derived implant of claim 1 possessing a total thickness of at least about 10 mm.

8. The bone-derived implant of claim 1 possessing a cross section for at least a portion of its length which is, or approximates, a circle, oval or polygon, the implant optionally possessing a cavity for at least a portion of its length.

9. The bone-derived implant of claim 8 wherein pores, apertures, perforations or channels provide communication between the cavity and the surface of the bone.

10. The bone-derived implant of claim 1 wherein at least one compression strength-imparting layer is provided as a multi-sectional bone section wherein subsections of bone constituting the section are joined to each other in edge-to-edge fashion.

11. The bone-derived implant of claim 1 wherein at least one compression strength-imparting later is provided as a multi-sectional bone section wherein subsections of bone constituting the section are joined to each other in edge-to-edge fashion.

12. The bone-derived implant of claim 1 possessing upper and lower major exposed surfaces, said surfaces being those of compression strength-imparting layers.

13. The bone-derived implant of claim 1 possessing at least one layer fabricated from a material selected from the group consisting of fully demineralized bone, graphite, pyrolytic carbon, hydroxyapatite, tricalcium phosphate, bioabsorbable material and nonbioabsorbable material.

14. The bone-derived implant of claim 1 wherein each strength-imparting layer possesses the same or different average thickness in the range of from about 0.5 mm to about 20 mm.

15. The bone-derived implant of claim 1 wherein each layer possesses the same or different average thickness in the range of from about 1.5 mm to about 15 mm.

16. The bone-derived implant of claim 5 wherein the at least two consecutive compression strength-imparting layers each possess a compression strength axis.

17. The bone-derived implant of claim 16 wherein the compression strength axis of the at least two consecutive compression strength-imparting layers are offset relative to each other.

18. The bone-derived implant of claim 17 wherein the at least two consecutive compression strength-imparting layers are each made up of spaced-apart sections with the compression strength axis of each of the layers being offset relative to each other in an arrangement defining an array of channels in all three dimensions.

19. The bone-derived implant of claim 1 having a compression strength of from about 25 to about 250 MPa.

20. The bone-derived implant of claim 1 having a compression strength of from about 100 to about 200 MPa.

21. The bone-derived implant of claim 1 possessing from 2 to about 200 layers.

22. The bone-derived implant of claim 13 possessing means for facilitating diffusion of bone healing material.

23. The bone-derived implant of claim 22 wherein the means for facilitating diffusion of bone healing material constitutes channels defined within one or more layers.

24. The bone-derived implant of claim 1 fabricated in whole or in part from cortical bone selected from the group consisting of allogenic and xenogenic.

25. The bone-derived implant of claim 1 containing at least one cavity.

26. The bone-derived implant of claim 25 wherein the cavity contains a material selected from the group consisting of collagen, antiviral agent, antimicrobial, antibiotic, angiogenic, antigenic agent and cytoskeletal agent.

27. The bone-derived implant of claim 1 wherein the adhesive is selected from the group consisting of cyanoacrylate, epoxy-based compound, dental resin sealant, dental resin cement, polymethylmethacrylate, gelatin-resorcinol-formaldehyde-glue, collagen-based glue, zinc phosphate, magnesium phosphate, zinc carboxylate and fibrin glue.

28. A method for treating a bone defect site which comprises:

providing a bone-derived implant which comprises a plurality of superimposed layers assembled with an adhesive into a unitary structure, at least one layer in the structure being a compression strength-imparting layer fabricated from nondemineralized cortical bone or partially demineralized cortical bone, and implanting the bone-derived implant at the bone defect site.

29. The method of claim 28 wherein the partially demineralized bone exhibits not less than about 40 percent of the compression strength of a comparable layer of fully mineralized bone.

30. The method of claim 29 wherein the partially demineralized bone exhibits not less than about 60 percent of the compression strength of a comparable layer of fully mineralized bone.

31. The method of claim 28 wherein the step of providing the bone-derived implant further comprises machining the bone-derived implant into a suitable bone configuration.

32. The method of claim 31 wherein the bone configuration is selected from the group consisting of ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones.

33. The bone-derived implant of claim 1 wherein the superimposed layers are assembled with mechanical fasteners.

* * * * *